(12) United States Patent
Marik

(10) Patent No.: US 8,518,114 B2
(45) Date of Patent: Aug. 27, 2013

(54) EXPANDABLE IMPLANT SYSTEM AND METHODS OF USE

(75) Inventor: Greg C. Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 151 days.

(21) Appl. No.: 13/091,685

(22) Filed: Apr. 21, 2011

(65) Prior Publication Data
US 2012/0271419 A1   Oct. 25, 2012

(51) Int. Cl.
*A61F 2/44* (2006.01)
(52) U.S. Cl.
USPC ........................................ 623/17.11
(58) Field of Classification Search
USPC .............. 623/17.11–17.16; 606/90
See application file for complete search history.

(56) References Cited

U.S. PATENT DOCUMENTS

| | | | |
|---|---|---|---|
| 3,875,595 A | 4/1975 | Froning | |
| 5,674,295 A | 10/1997 | Ray et al. | |
| 6,969,404 B2 | 11/2005 | Ferree | |
| 7,507,241 B2 * | 3/2009 | Levy et al. | 606/60 |
| 7,758,644 B2 | 7/2010 | Trieu | |
| 8,187,327 B2 * | 5/2012 | Edidin et al. | 623/17.11 |
| 2002/0147496 A1 | 10/2002 | Belef et al. | |
| 2004/0133280 A1 * | 7/2004 | Trieu | 623/17.16 |
| 2004/0249461 A1 | 12/2004 | Ferree | |
| 2006/0247778 A1 | 11/2006 | Ferree et al. | |
| 2007/0093899 A1 * | 4/2007 | Dutoit et al. | 623/17.11 |
| 2010/0249933 A1 | 9/2010 | Trieu | |

* cited by examiner

*Primary Examiner* — Mary Hoffman

(57) ABSTRACT

A spinal implant includes a first component including a first surface configured for engagement with a first vertebral surface and a second surface configured to define at least a portion of an implant support cavity. A second component is connected to the first component and includes a first surface configured for engagement with a second vertebral surface and a second surface configured to define at least a portion of the implant support cavity. A removable intermediate component is configured for disposal in the implant support cavity. The intermediate component is inflatable to move the first component relative to the second component to expand the interbody implant from a first configuration to a second, expanded configuration. At least one agent is configured to replace the intermediate component in the implant support cavity in the second configuration. Methods of use are disclosed.

17 Claims, 9 Drawing Sheets

EXPANDABLE IMPLANT SYSTEM AND METHODS OF USE

TECHNICAL FIELD

The present disclosure generally relates to medical devices, systems and methods for the treatment of musculoskeletal disorders, and more particularly to an interbody implant system and method that provides stabilization and height restoration for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY OF THE INVENTION

Accordingly, an interbody implant system and method is provided that provides stabilization and height restoration for treating a vertebral column. It is contemplated that the interbody implant system includes a spinal implant, which is expandable between a first configuration and a second configuration. It is further contemplated that the implant system and method may be employed for an arthrodesis treatment using minimally invasive and percutaneous techniques.

In one embodiment, a spinal implant is provided. The spinal implant includes a first component including a first surface configured for engagement with a first vertebral surface and a second surface configured to define at least a portion of an implant support cavity. A second component is connected to the first component. The second component includes a first surface configured for engagement with a second vertebral surface and a second surface configured to define at least a portion of the implant support cavity. A removable intermediate component is configured for disposal in the implant support cavity. The intermediate component is inflatable such that the first component and the second component expand from a first configuration to a second, expanded configuration. At least one agent is configured to replace the intermediate component in the implant support cavity in the second configuration.

In one embodiment, an interbody implant system is provided. The interbody implant system includes a spinal implant. The spinal implant includes a first arm extending between a first end and a second end, and includes a first vertebral engaging surface. A second surface defines a recessed portion and a remaining planar portion. A second arm is extendable between a first end and a second end. The first end of the second arm is connected to the first end of the first arm. The second arm includes a first vertebral engaging surface and a second surface defining a recessed portion and a remaining planar portion. An implant support cavity is defined by the recessed portions of the first and the second arms. A removable balloon is configured for disposal in the implant support cavity. The balloon is inflatable such that the first arm and the second arm expand from a collapsed configuration to an expanded configuration. The balloon is collapsible from the expanded configuration for removal. A pressured fluid source is connectable to the balloon. At least one agent is configured to replace the balloon in the implant support cavity.

In one embodiment, a method for treating a spine is provided. The method for treating the spine includes the steps of providing an interbody implant, similar to those described herein; disposing the intermediate component in the implant support cavity; disposing the interbody implant between a first vertebral surface and a second vertebral surface in a collapsed configuration such that the first surface of the first component engages the first vertebral surface and the first surface of the second component engages the second vertebral surface; expanding the balloon such that the first component and the second component expand to an expanded configuration; and removing the balloon from the implant support cavity.

BRIEF DESCRIPTION OF THE DRAWINGS

The present disclosure will become more readily apparent from the specific description accompanied by the following drawings, in which.

DETAILED DESCRIPTION OF THE INVENTION

Figure 1:
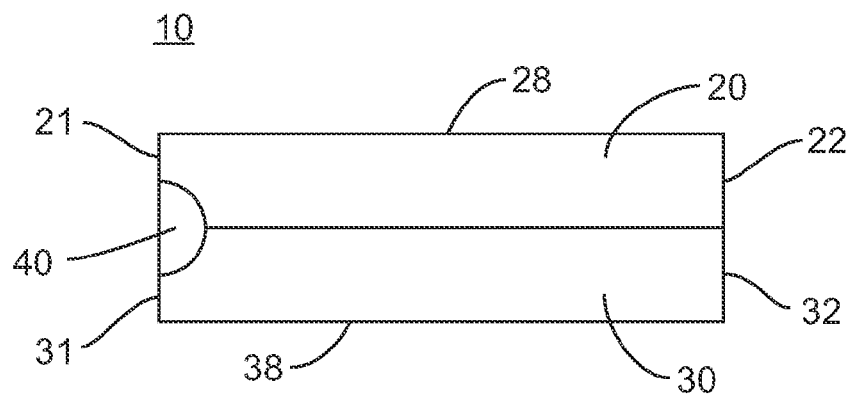
FIG. 1 is a side view of one particular embodiment of a spinal implant of a system in accordance with the principles of the present disclosure.
Figure 2:
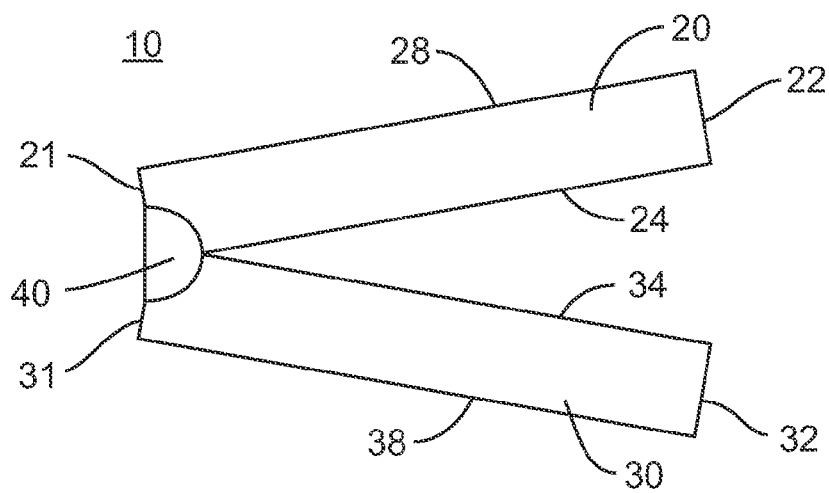
FIG. 2 is a side view of the spinal implant shown in FIG. 1.
Figure 3:
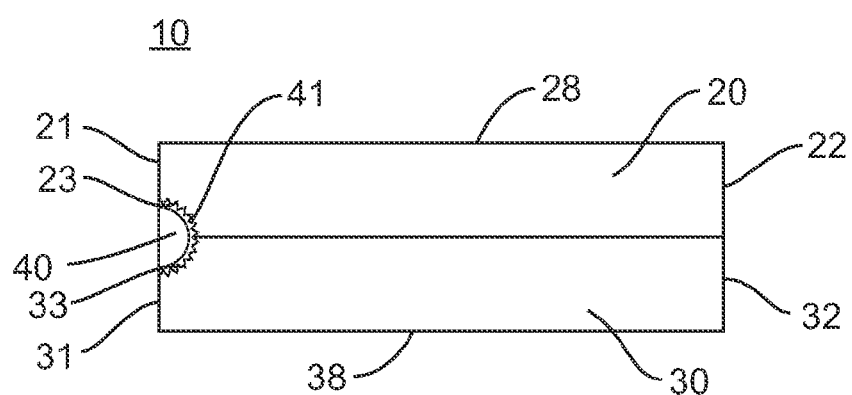
FIG. 3 is an enlarged side view of the spinal implant shown in FIG. 1.
Figure 4:
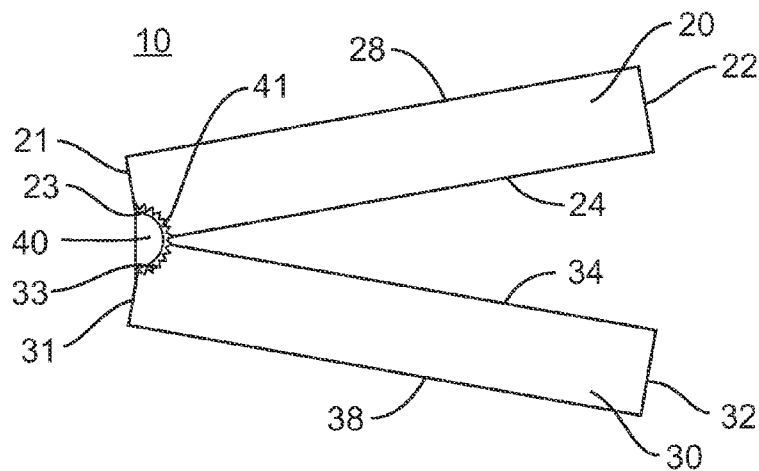
FIG. 4 is an enlarged side view of the spinal implant shown in FIG. 1.
Figure 5:
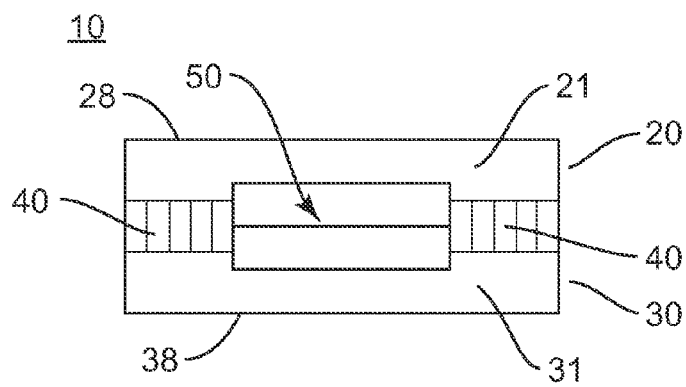
FIG. 5 is a rear view of the spinal implant shown in FIG. 1.
Figure 6:
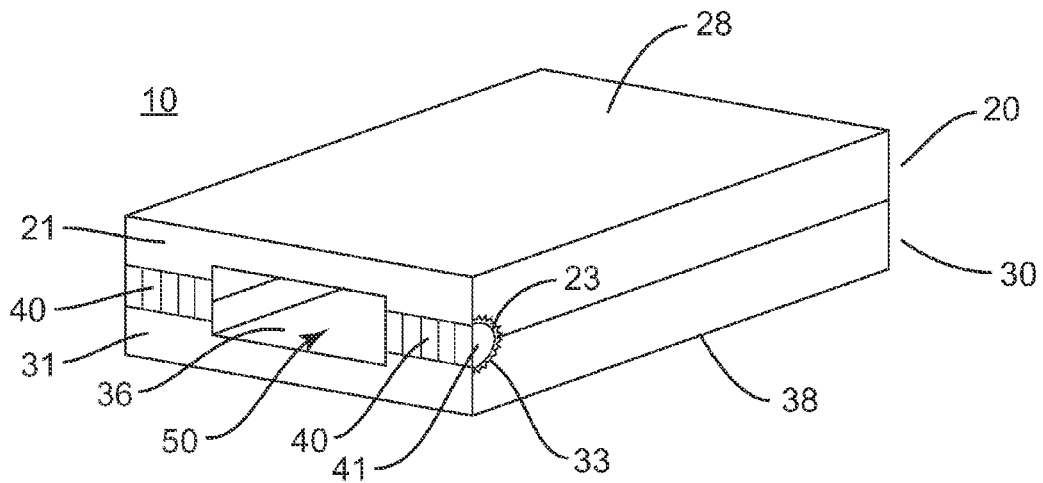
FIG. 6 is a perspective view of the spinal implant shown in FIG. 1.
Figure 7:
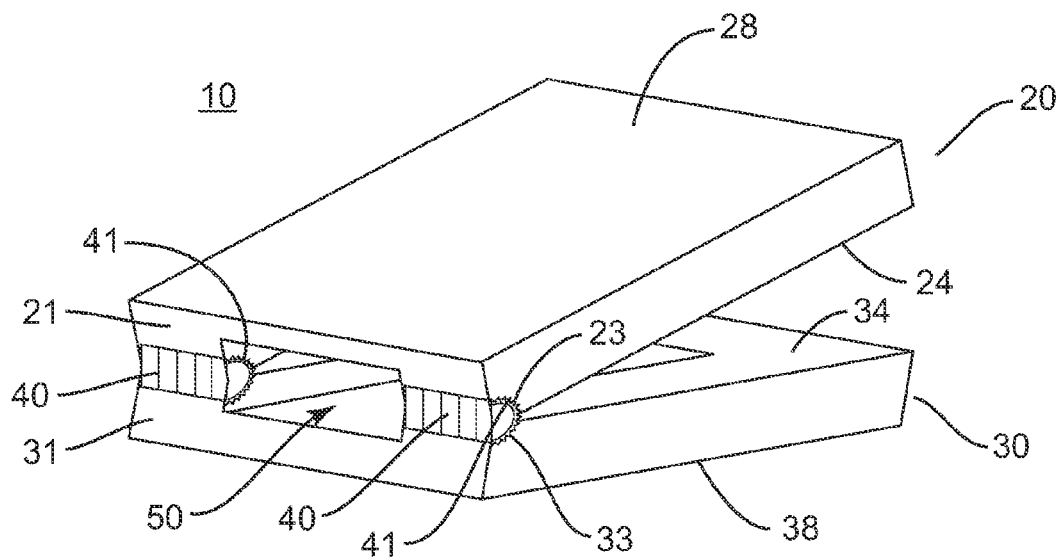
FIG. 7 is a perspective view of the spinal implant shown in FIG. 1.
Figure 8:
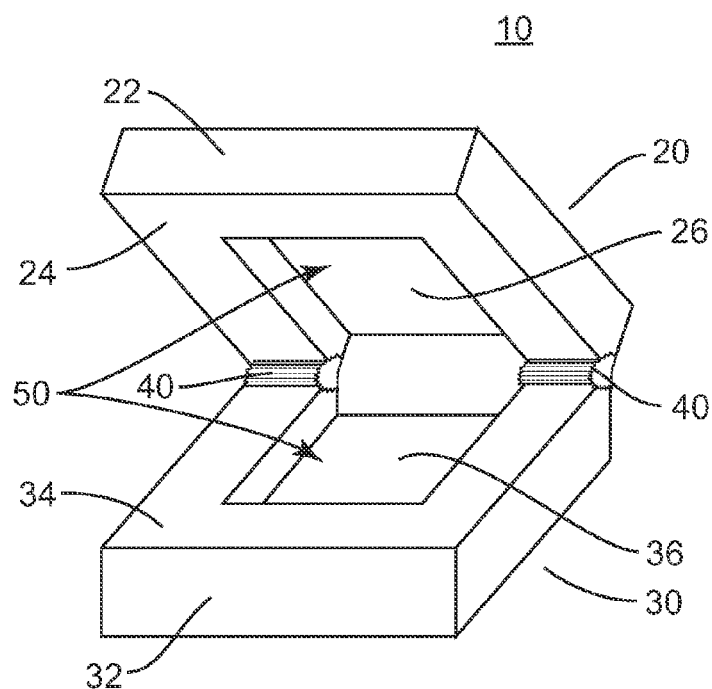
FIG. 8 is a perspective view of the spinal implant shown in FIG. 1.

The exemplary embodiments of the interbody implant system and related methods of use disclosed are discussed in terms of medical devices for the treatment of musculoskeletal disorders and more particularly, in terms of an interbody implant that provides stabilization and height restoration for treating a vertebral column. It is envisioned that the interbody implant system may be employed for fusion and fixation treatments. It is further envisioned that the interbody implant system and methods of use disclosed can be employed to obtain fusion of vertebrae through a minimally invasive or percutaneous technique. In one embodiment, the disclosed interbody implant system and methods of use can provide improved spinal treatment with a device that expands to achieve decompression and the restoration of lordosis.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed interbody implant system may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The present disclosure may also be alternatively employed with procedures for treating the lumbar, cervical, thoracic and pelvic regions of a spinal column. The interbody implant system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an interbody implant, and interbody implant system and related methods of employing the interbody implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-19, there is illustrated components of an interbody implant system in accordance with the principles of the present disclosure.

The components of the interbody implant system can be fabricated from biologically acceptable materials suitable for medical applications, including metals, synthetic polymers, ceramics and bone material and/or their composites, depending on the particular application and/or preference of a medical practitioner. For example, the components of the interbody implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), amorphous metals, ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the interbody implant system may have material composites, including the above materials, to achieve various desired characteristics such as strength, rigidity, elasticity, compliance, biomechanical performance, durability and radiolucency or imaging preference. The components of the interbody implant system, individually or collectively, may also be fabricated from a heterogeneous material such as a combination of two or more of the above-described materials.

The interbody implant system includes a spinal implant 10 employed as a stabilization device in fusion and fixation procedures, for example, for patients suffering from a spinal disorder to provide height restoration between vertebral bodies, decompression and/or restoration of lordosis. The components of the interbody implant system may be monolithically formed, integrally connected or include fastening elements and/or instruments, for example, as described herein.

Spinal implant 10 includes a first component, such as, for example, a first arm 20 extending between a first end 21 and a second end 22. Arm 20 includes locking teeth 23. Spinal implant 10 includes a second component, such as, for example, a second arm 30 extending between a first end 31 and a second end 32. Arm 30 includes locking teeth 33. Spinal implant 10 includes a hinge 40 pivotably connecting first arm 20 to second arm 30. Hinge 40 includes locking teeth 41. It is envisioned that arms 20, 30 may be monolithically formed or alternatively connected by integral connection, press fit, threaded, adhesive and/or fastening elements such as clip and/or screws. Teeth 23, 33 are configured to engage and mesh with teeth 41 in a locking configuration to maintain arm 20 in a fixed orientation with respect to arm 30 between and including a first configuration and a second configuration, as discussed below. It is contemplated that spinal implant 10 may employ alternate mechanisms to maintain arms 20, 30 in a particular fixed orientation. For example, in one embodiment, arms 20, 30 are connected by a hinge, which may include pivoting plates connected with a pin, separate articulating components and/or a living hinge. In one embodiment, the hinge includes a first plate connected to arm 20 and a second plate connected to arm 30 such that at least one of the first and second plates are disposed in a horizontal orientation in the first configuration and the plate then rotates to a vertical fixed orientation in the second configuration. In one embodiment, the hinge can include a pin disposed adjacent the connection of arms 20, 30 in an anterior orientation with the plates disposed in a posterior orientation. The pin is engageable to expand arms 20, 30.

Arms 20, 30 each have a rectangular cross section configuration and are disposed in a substantially parallel orientation relative to each other in a first configuration, described below. It is envisioned that arms 20, 30 may extend in alternate configurations such as, for example, alternative radius of curvature, linear, offset and/or staggered. It is further envisioned that arms 20, 30 may have alternate cross section configurations, such as, for example, oval, oblong, triangular, rectangular, square, polygonal, irregular, uniform, non-uniform, variable, hollow and/or tapered.

Arms 20, 30 include outer surfaces 28, 38. Surfaces 28, 38 are substantially smooth or even. It is envisioned that all or only a portion of surfaces 28, 38 may have alternate surface configurations, such as, for example, rough, arcuate, undulating, mesh, porous, semi-porous, dimpled, polished and/or textured according to the requirements of a particular application. Surfaces 28, 38 are vertebra engaging surfaces, which can include a plurality of raised elements configured to enhance fixation and/or gripping with vertebral tissue. It is envisioned that surfaces 28, 38 may have alternate surface configurations to enhance fixation with tissue such as those alternatives described herein.

Arms 20, 30 include surfaces 24, 34 that define recessed portions, such as, for example, recesses 26, 36, discussed below, that define an inner cavity 50. The remaining portions of surfaces 24, 34 each include planar portions that are substantially smooth or even, and facilitate abutting engagement of arms 20, 30 and a low profile configuration of spinal implant 10 in a collapsed configuration, as will be described. It is envisioned that all or only a portion of surfaces 24, 34 may have alternate surface configurations, such as, for example, rough, arcuate, undulating, mesh, porous, semi-porous, dimpled, polished and/or textured according to the requirements of a particular application. Cavity 50 expands and collapses with spinal implant 10, as will be described. It is contemplated that cavity 50 may have alternate cross section configurations such as those alternatives described herein.

Arms 20, 30 include opposing recesses 26, 36 that create cavity 50. Recesses 26, 36 extend through ends 21, 31. Recesses 26, 36 are shown to not extend though ends 22, 32, but in alternate embodiments can also extend though ends 22, 32. Recesses 26, 36 each have a rectangular cross section configuration and are disposed in a substantially parallel orientation relative to each other in the first configuration, described below. It is envisioned that recesses 26, 36 may extend in alternate configurations such as, for example, arcuate, offset and/or staggered. It is further envisioned that recesses 26, 36 may have alternate cross section configurations, such as, for example, oval, oblong, triangular, square, polygonal, irregular, uniform, non-uniform, variable, hollow and/or tapered.

A removable intermediate component, such as, for example, an inflatable body 60 is engageable with arm 20 and arm 30. It is envisioned that inflatable body 60 includes a balloon, inflatable membrane or member having fluid seal that is configured to expand with inflation by a pressurized expanding medium. Body 60 is disposed with arms 20, 30 such that at least a portion of body 60 is disposed within recesses 26, 36. Body 60 defines a first surface 61 configured for engagement with recess 26 and a second surface 62 configured for engagement with recess 36. Body 60 also defines side surfaces 63, 64, which have a substantially arcuate configuration in the expanded configuration, discussed below. Surfaces 61-64 have a substantially smooth configuration. It is envisioned that all or only a portion of each of surfaces 61-64 may have alternate surface configurations, such as, for example, arcuate, undulating, rough, semi-porous, dimpled and/or textured. It is further envisioned that body 60 has an overall diameter D and height H, in the expanded configuration discussed below. It is contemplated that diameter D may be in a range of 10 to 40 millimeters (mm). It is further contemplated that height H may be in a range of 8 to 24 mm.

Figure 9:
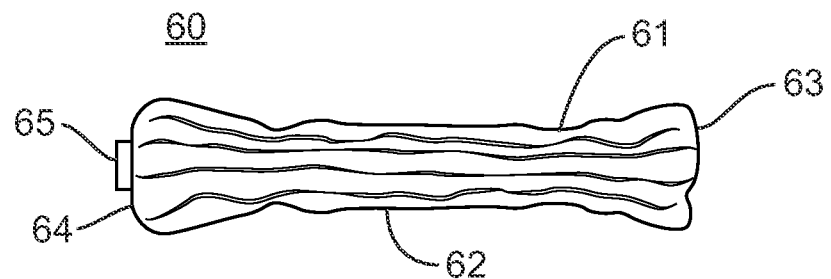
FIG. 9 is a side view of an intermediate component of a system in accordance with the principles of the present disclosure.
Figure 10:
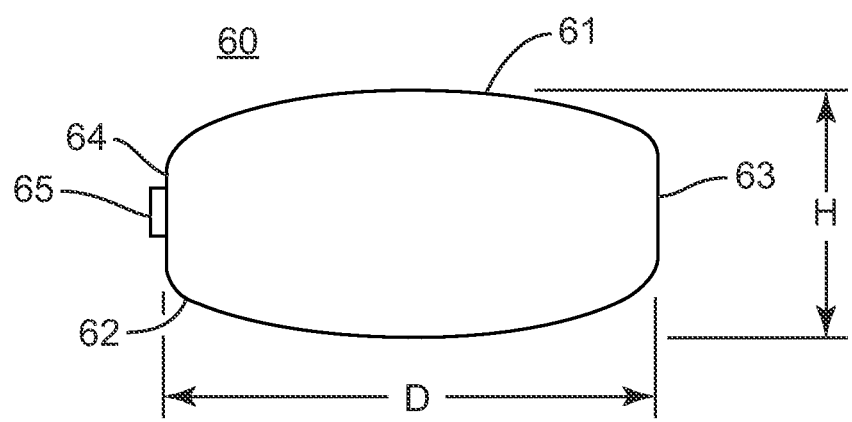
FIG. 10 is a side view of the intermediate component shown in FIG. 9.
Figure 11:
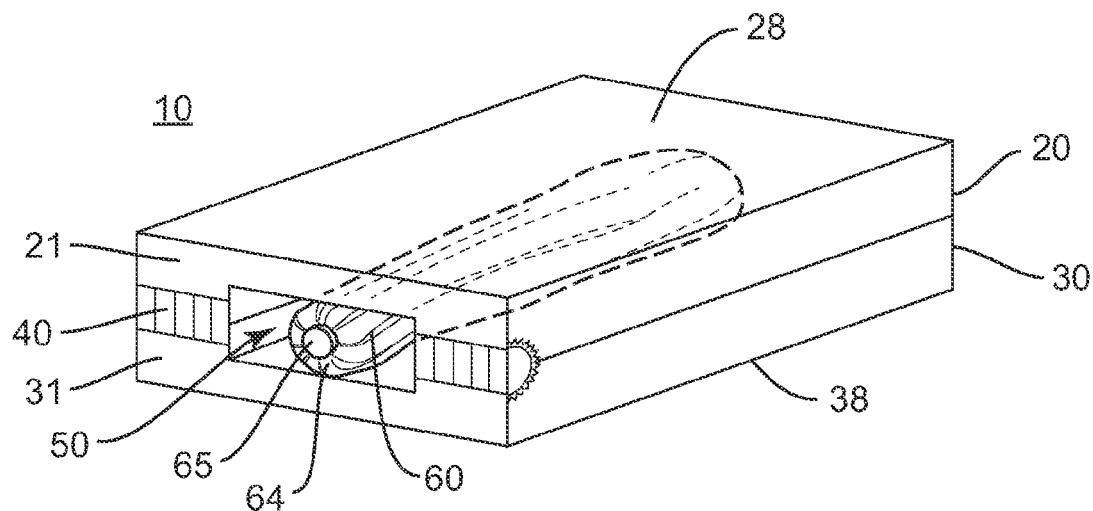
FIG. 11 is a perspective view of a system in accordance with the principles of the present disclosure.
Figure 12:
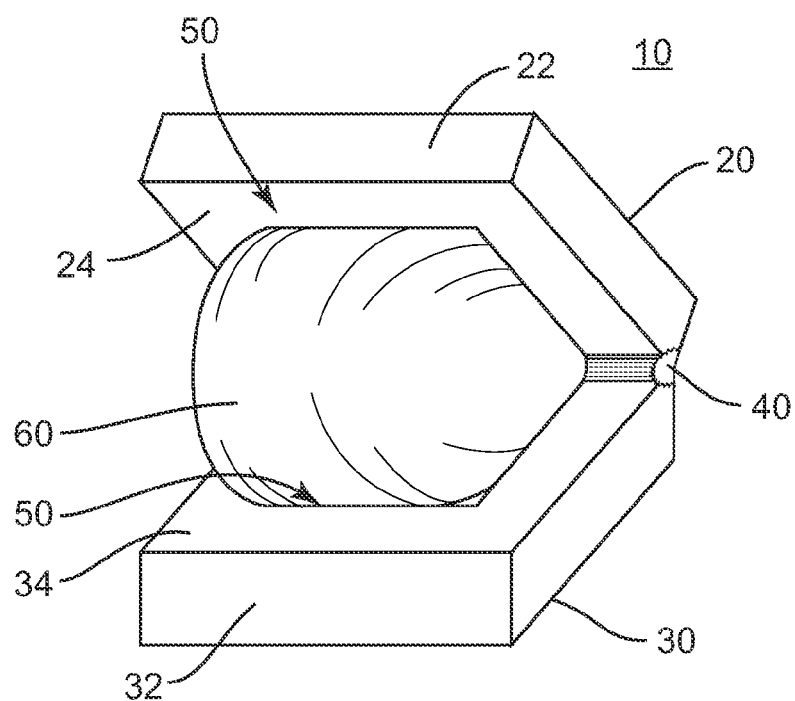
FIG. 12 is a perspective view of the system shown in FIG. 11.

Body 60 is expandable from a first, non-expanded configuration (FIG. 9). Body 60 defines a cavity, such as, for example, an inflatable chamber configured for receiving a pressurized expanding medium to expand body 60 to a second, expanded configuration (FIG. 10). It is envisioned that body 60 may define one or a plurality of cavities configured for receiving a pressurized expanding medium, which may or may not be in communication and/or separately expandable. It is envisioned that body 60 may be alternately configured in other shapes such as those described herein.

Body 60 is disposed within implant 10 in cavity 50. Body 60 and implant 10 are expandable from a first, non-expanded configuration (FIG. 11) such that surfaces 24, 34 of arms 20, 30 are disposed in an abutting engagement to provide a low profile configuration of implant 10 to a second, expanded configuration (FIG. 12) such that at least a portion of surfaces 24, 34 are spaced apart and arm 20 is rotated relative to arm 30 such that implant 10 is expanded for engaging tissue, for example, vertebral endplates. It is contemplated that expansion and/or relative movement of arms 20, 30 to expand implant 10 from the first configuration to the second configuration includes parallel expansion of arms 20, 30, expansion of arms 20, 30 at a relative angular orientation, relative rotation of arms 20, 30, relative pivotal movement of arms 20, 30, inflation, distention, swelling and/or linear translation.

The interbody implant system includes an injection conduit, such as, for example, lumen 110 (FIG. 15) communicating with inflatable chamber via a valve 65 of body 60. Lumen 110 is connected to a source 112 of pressurized expanding medium, such as, for example, inflating air, gas, fluid, and/or injectable polymer. Lumen 110 is configured to introduce the pressurized expanding medium from source 112 into the inflatable chamber to expand body 60 to the second, expanded configuration. It is contemplated that the pressurized expanding medium is introduced at a pressure in a range of 3 pounds per square inch (psi) to 5000 psi. The pressurized flow may be constant or varied, depending on the application, and can be measured by gauge 108. It is contemplated that alternative pressurized expanding mediums may be employed such as sterile water or saline.

Source 112 may be a syringe barrel with plunger, pressurized container and/or wall connection. The flow and/or pressure may be regulated and/or valve controlled manually, electronically or processor controlled, as is known to one skilled in the art. It is envisioned that body 60 may be fabricated from biologically acceptable materials including vinyl, polyvinyl chloride, silicone, nylon, thermoplastic rubbers, thermoplastic elastomer materials, polyethylenes, ionomer, polyurethane, polyolefins, polyetheretherketone, polyactide, polyglycolide, poly(lactide-co-glycolide), poly(dioxanone), poly(ε-caprolactone), poly(hydroxylbutyrate), poly(hydroxylvalerate), tyrosine-based polycarbonate, polypropylene fumarate, polyethylene tetraphthalates (PET), or combinations thereof. Body 60 may be constructed of materials to achieve various desired characteristics such as biocompatibility, strength, thickness, rigidity, elasticity, durability, and/or permeability. It is envisioned that body 60 in the first or second configuration may have various cross section configurations, such as, for example, those alternatives described herein.

In assembly, operation and use, the interbody implant system is employed with a surgical procedure such as a fusion treatment of a spine of a patient including vertebrae V, intervertebral disc space I and body areas adjacent thereto, as discussed herein. The interbody implant system may also be employed with other surgical procedures, such as, for example, discectomy, laminotomy, laminectomy, nerve root retraction, foramenotomy, facetectomy, decompression, and spinal, nucleus or disc replacement.

For example, the interbody implant system can be employed with a surgical procedure to provide height restoration between vertebral bodies for treatment of an applicable condition or injury of an affected section of a spinal column and adjacent areas within a body, such as, for example, intervertebral disc space I between the endplate of vertebrae V1 and the endplate of vertebrae V2 of vertebrae V. It is contemplated that implant 10 of the interbody implant system can be inserted with intervertebral disc space I to space apart articular joint surfaces, provide support and maximize stabilization of vertebrae V.

In use, as shown in FIGS. 13-19, to treat the affected section of vertebrae V, a medical practitioner obtains access to a surgical site including vertebrae V in any appropriate manner, such as through incision and retraction of tissues. It is envisioned that implant 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Implant 10 is then employed to augment the surgical treatment. It is contemplated that one or all of the components of implant 10 can be delivered to the surgical site via manual manipulation and/or a free hand technique. It is further contemplated that implant 10 may be inserted posteriorly, and then manipulated anteriorly and/or lateral and/or medial.

Figure 13:
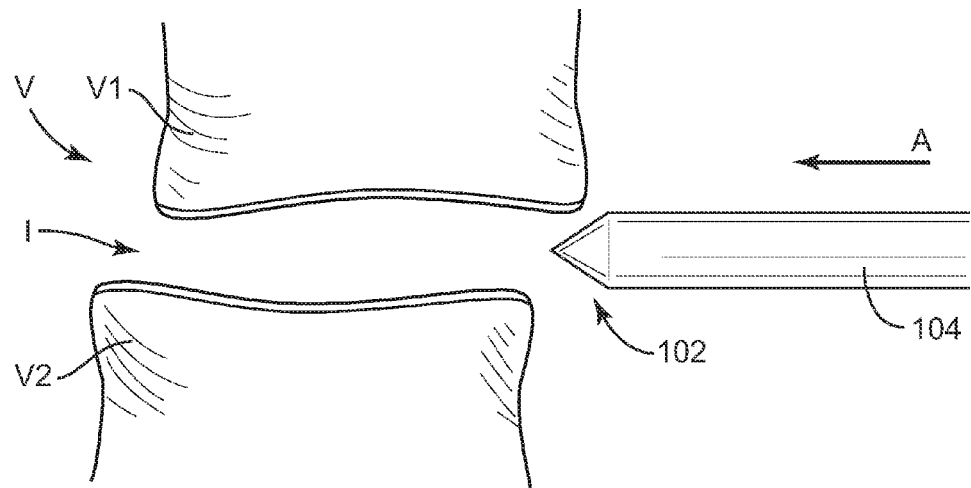
FIG. 13 is a side view of vertebrae and a component of the system shown in FIG. 11.
Figure 14:
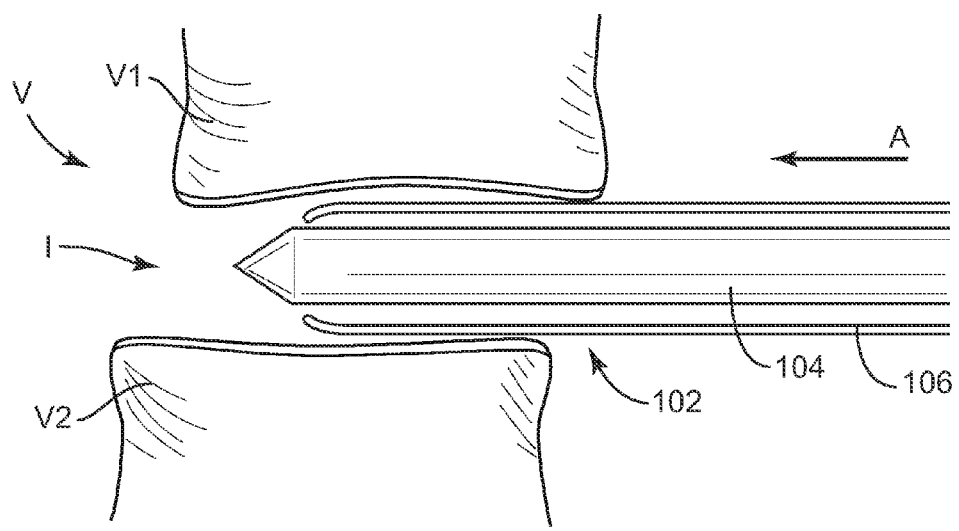
FIG. 14 is a side view of the vertebrae and the system shown in FIG. 11.

An incision is made in the body of a patient and a cutting instrument (not shown) creates a surgical pathway 102 for implantation of implant 10 within the patient body, as shown in FIG. 13. A guide instrument 104 is employed to initially distract vertebrae V1 from vertebrae V2, as manipulated in the direction of arrow A. A sleeve or cannula 106 is used to access intervertebral disc space I, as manipulated in the direction of arrow A shown in FIG. 14, and facilitate delivery and access for components of the interbody implant system. A preparation instrument (not shown) can be inserted within cannula 106 and disposed within intervertebral disc space I. The preparation instrument(s) can be employed to remove some or all of the disc tissue including the disc nucleus and fluids, adjacent tissues and/or bone, corticate, scrape and/or remove tissue from the surfaces of endplates of opposing vertebrae V1, V2, as well as for aspiration and irrigation of the region according to the requirements of a particular surgical application.

Figure 15:
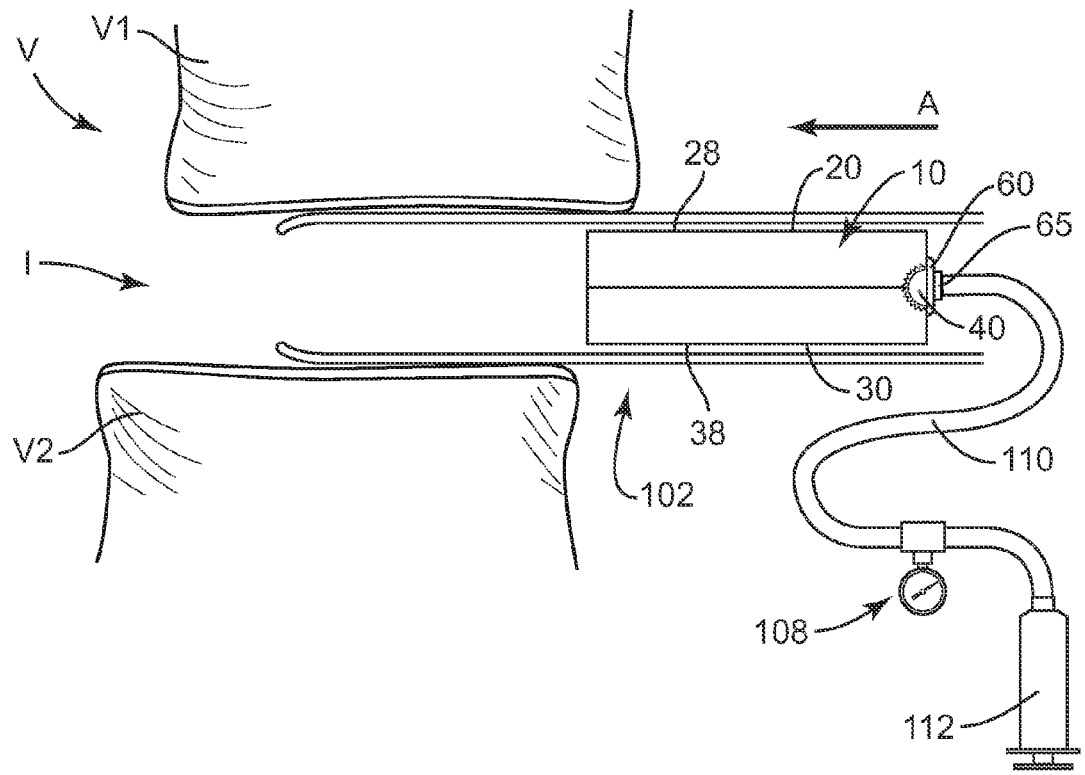
FIG. 15 is a side view of the vertebrae and the system shown in FIG. 11.
Figure 16:
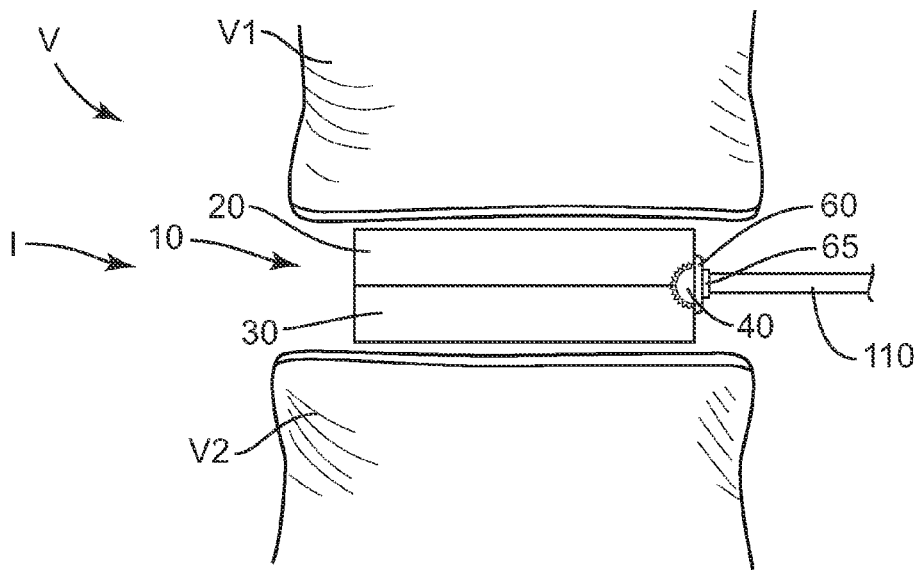
FIG. 16 is a side view of the vertebrae and the system shown in FIG. 15.

Implant 10, with body 60 disposed therein, in the first, non-expanded configuration, discussed above, is delivered through surgical pathway 102, as shown in FIG. 15, into intervertebral disc space I with a delivery instrument (not shown) including a driver (not shown) via sleeve 106, as manipulated in the direction of arrow A. The driver delivers implant 10 into the prepared intervertebral disc space I, between vertebrae V1 and vertebrae V2, according to the requirements of a particular surgical application. Implant 10 is manipulated such that opposing surfaces 28, 38 of implant 10 will engage endplates of opposing vertebrae V1, V2 upon inflation of body 60, as shown in FIG. 16.

Lumen 110 communicates with inflatable chamber via valve 65, as described above. Lumen 110 is connected to source 112, as regulated by gauge 108, which supplies pressurized expanding medium into the inflatable chamber to expand body 60 to the second, expanded configuration. According to the particular surgical application, gauge 108 is set to a particular pressure, similar to those described above, and inflatable chamber is filled with the pressurized expanding medium at that pressure and body 60 is inflated and arms 20, 30 of implant 10 are expanded to a desired configuration. Surfaces 24, 34 are spaced apart and arm 20 is rotated relative to arm 30 such that implant 10 is expanded to the second, expanded configuration.

Figure 17:
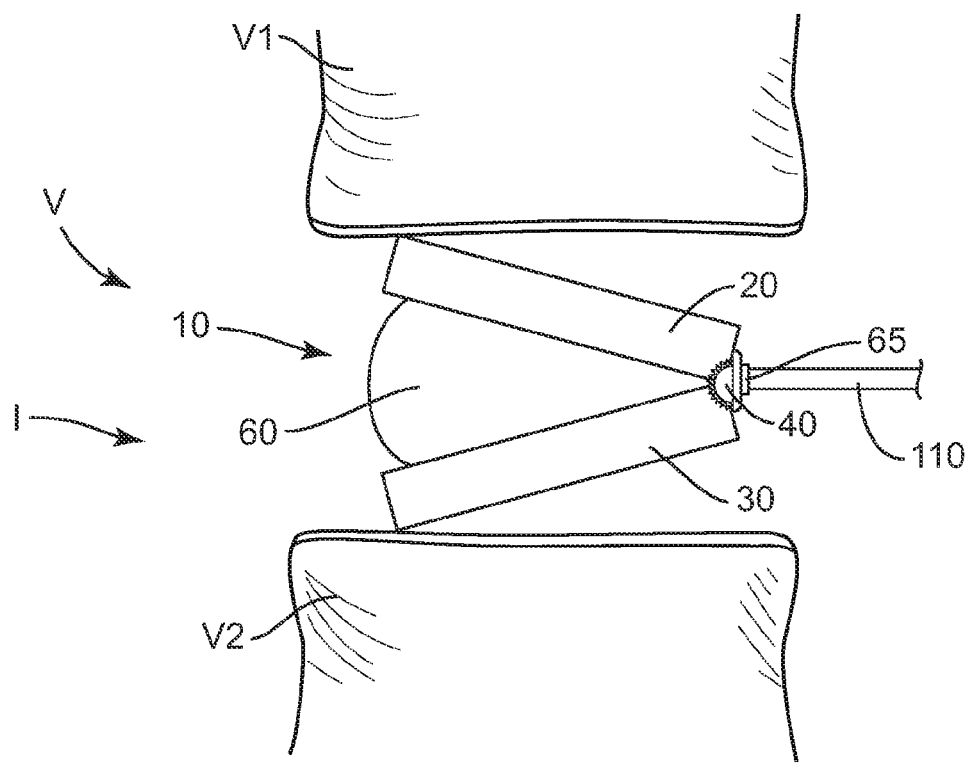
FIG. 17 is a side view of the vertebrae and the system shown in FIG. 15.
Figure 18:
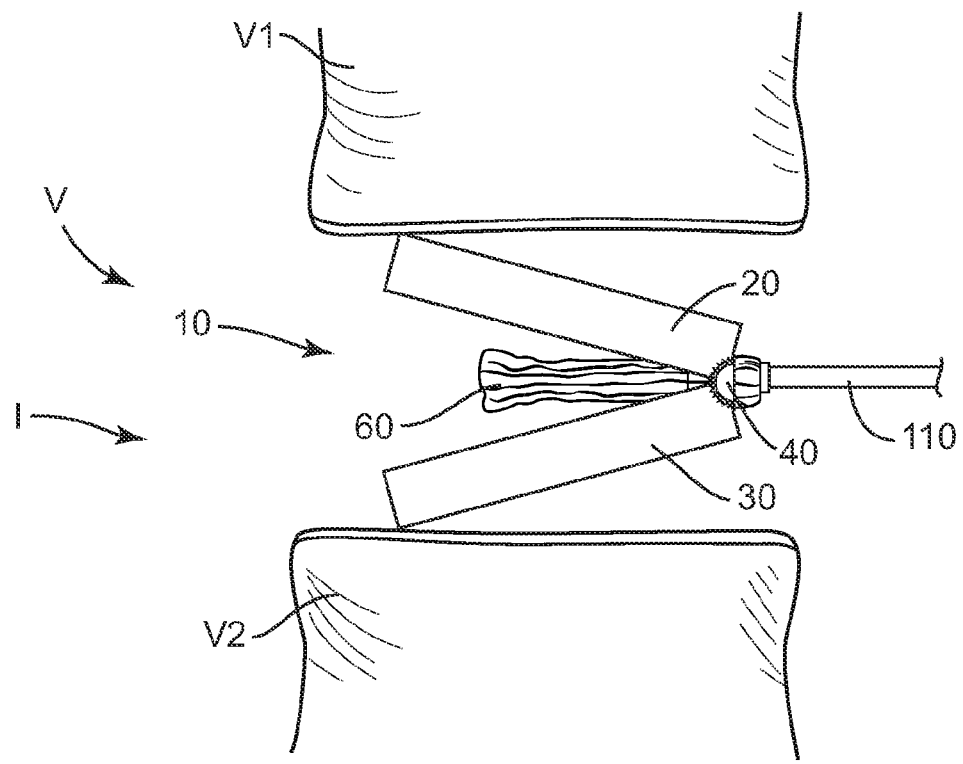
FIG. 18 is a side view of the vertebrae and the system shown in FIG. 15.
Figure 19:
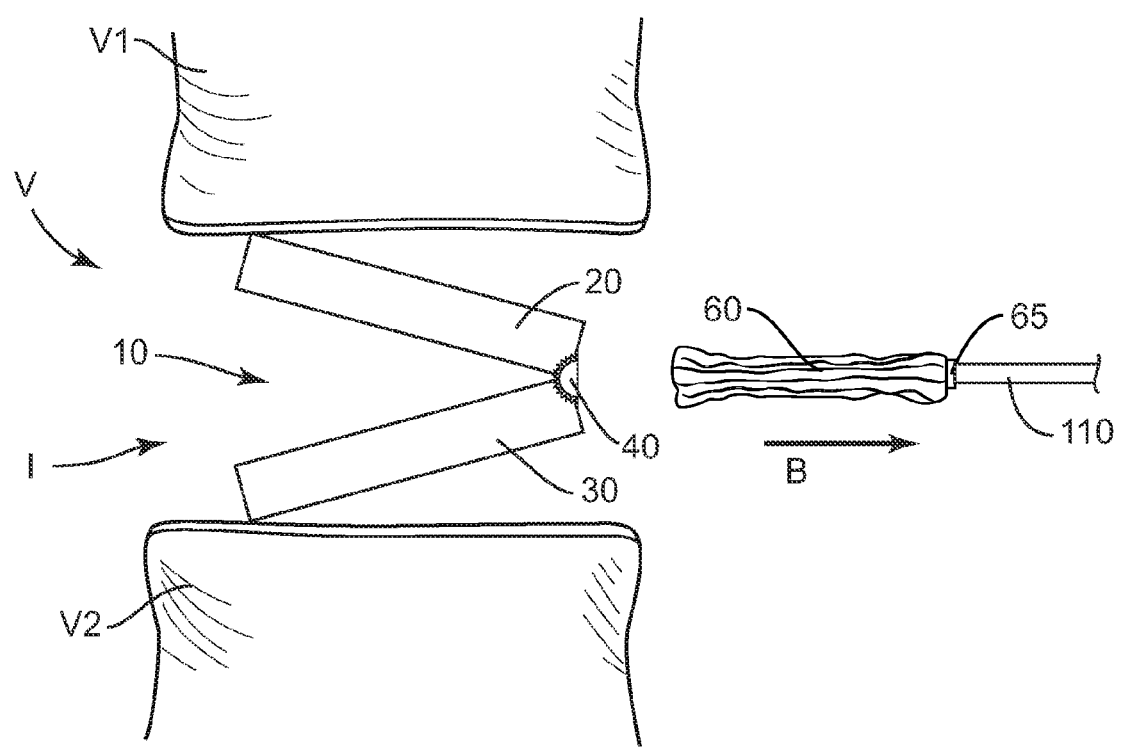
FIG. 19 is a side view of the vertebrae and the system shown in FIG. 15.

In the second, expanded configuration, as shown in FIG. 17, arm 20 extends outwardly in a configuration to engage the endplate of vertebrae V1, and arm 30 extends outwardly in a configuration to engage the endplate of vertebrae V2. After arms 20, 30 are extended outwardly and are locked into position via teeth 23, 33 and 41, discussed above, body 60 is deflated, as shown in FIG. 18, by applying a negative pressure through lumen 110 and valve 65. This negative pressure deflates body 60 leaving arms 20, 30 in their locked and expanded position. Deflated body 60 is then removed from cavity 50, as shown in FIG. 19, and from the surgical site in the direction shown by arrow B.

Implant 10 remains in place within disc space I and in engagement with vertebrae V1, V2 to stabilize the area of vertebrae V in accordance with the surgical procedure. The components of implant 10 secure and stabilize vertebrae V in connection with the surgical procedure while preventing undesired migration of implant 10. It is envisioned that one or a plurality of implants 10 may be used for a surgical procedure employing the interbody implant system. It is further envisioned that the plurality of implants 10 can be variously sized and configured, and/or oriented in a side by side engagement, spaced apart and/or staggered. Implant 10 can be made of radiolucent materials such as polymers. Radiomarkers may be included for identification under x-ray, fluoroscopy, CT or other imaging techniques.

In one embodiment, subsequent to removal of body 60 from cavity 50, the interbody implant system includes at least one agent. The agent is configured to replace body 60 within cavity 50 in the expanded configuration. The agent is delivered through surgical pathway 102 (FIG. 15) into disc space I with a delivery instrument (not shown) via sleeve 106 and is disposed, packed or layered within, on or about the components and/or surfaces of implant 10, disc space I, vertebrae V and/or the surgical site. It is contemplated that the agent may include bone growth promoting material, such as, for example, bone graft. The bone graft can be a particulate material, which may include an osteoconductive material such as hydroxyapatite and/or an osteoinductive agent such as a bone morphogenic protein to enhance bony fixation of implant 10 with the adjacent areas of vertebrae V.

It is contemplated that the bone graft may include therapeutic polynucleotides or polypeptides. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, Growth and Differentiation Factors proteins (GDF) and cytokines.

It is envisioned that the agent may include one or a plurality of therapeutic agents and/or pharmacological agents for release, including sustained release, to treat, for example, pain, inflammation and degeneration. The agent may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An interbody implant comprising:
 a first component including locking teeth, a first surface configured for engagement with a first vertebral surface and a second surface configured to define at least a portion of an implant support cavity;
 a second component connected to the first component, the second component including locking teeth, a first surface configured for engagement with a second vertebral surface and a second surface configured to define at least a portion of the implant support cavity;
 a hinge including locking teeth, the hinge connecting the first component with the second component;
 a removable intermediate component configured for disposal in the implant support cavity, the intermediate component being inflatable to move the first component relative to the second component to expand the interbody implant from a first configuration to a second, expanded configuration in which the locking teeth on the hinge mesh with and engage the locking teeth on the first and components to maintain the interbody implant in the second, expanded configuration; and
 at least one agent configured to replace the intermediate component in the implant support cavity in the second configuration.

2. An interbody implant according to claim 1, wherein the first component is pivotably connected to the second component with the hinge.

3. An interbody implant according to claim 1, wherein the first component and the second component are monolithically formed.

4. An interbody implant according to claim 1, wherein the first component and the second component are fixable in the second, expanded configuration.

5. An interbody implant according to claim 1, wherein the second surface of the first component further defines a planar surface configured to engage the second surface of the second component in the first configuration.

6. An interbody implant according to claim 1, wherein the implant support cavity has a rectangular cross section configuration.

7. An interbody implant according to claim 1, wherein the intermediate component includes a balloon.

8. An interbody implant according to claim 1, wherein the at least one agent includes at least one of bone graft and at least one pharmaceutical.

9. An interbody implant according to claim 1, wherein the intermediate component is configured for deflation from the second configuration.

10. An interbody implant according to claim 1, wherein the intermediate component is collapsible within the implant support cavity for removal therefrom.

11. An interbody implant system comprising:
- a first arm extending between a first end and a second end, and including a plurality of splines, a first vertebral engaging surface and a second surface defining a recessed portion and a remaining planar portion;
- a second arm extending between a first end and a second end, the first end of the second arm being pivotably connected to the first end of the first arm, the second arm including a plurality of splines, a first vertebral engaging surface and a second surface defining a recessed portion and a remaining planar portion;
- a hinge including a plurality of splines, the hinge connecting the first arm with the second arm;
- an implant support cavity being defined by the recessed portions of the first and the second arms; a removable balloon configured for disposal in the implant support cavity, the balloon being inflatable to rotate the first arm relative to the second arm from a collapsed configuration to an expanded configuration in which the splines of the hinge mesh with and engage the splines of the arms to maintain the implant in the expanded configuration, the balloon being collapsible from the expanded configuration for removal;
- a pressured fluid source connected to the balloon; and
- at least one agent configured to replace the balloon in the implant support cavity.

12. An interbody implant system according to claim 11, wherein the first arm is pivotably connected to the second arm with the hinge.

13. An interbody implant system according to claim 11, wherein the first arm and the second arm are fixable in the expanded configuration.

14. An interbody implant system according to claim 11, wherein the planar portions of the first arm and second arm are configured for abutting engagement in the collapsed configuration.

15. An interbody implant system according to claim 11, wherein the at least one agent includes at least one of bone graft and at least one pharmaceutical.

16. An interbody implant system according to claim 11, wherein the firs t arm is pivotably connected to the second arm by the hinge, wherein the hinge is a living hinge.

17. An interbody implant system according to claim 11, wherein the second ends of the first and the second arms define a fluid port configured to support a connection between the balloon and the pressurized fluid source.

* * * * *